United States Patent
Hazard et al.

(10) Patent No.: US 9,364,194 B2
(45) Date of Patent: Jun. 14, 2016

(54) SYSTEMS AND METHODS FOR DETECTING REGIONS OF ALTERED STIFFNESS

(75) Inventors: Christopher Robert Hazard, Niskayuna, NY (US); Feng Lin, Nikayuna, NY (US); Mirsaid Seyed Bolorforosh, Albany, NY (US); Kenneth Wayne Rigby, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 2234 days.

(21) Appl. No.: 12/212,903

(22) Filed: Sep. 18, 2008

(65) Prior Publication Data
US 2010/0069751 A1    Mar. 18, 2010

(51) Int. Cl.
- *A61B 8/00* (2006.01)
- *A61B 5/00* (2006.01)
- *A61B 8/08* (2006.01)
- *G01S 7/52* (2006.01)
- *G01S 15/10* (2006.01)

(52) U.S. Cl.
CPC . *A61B 8/00* (2013.01); *A61B 5/415* (2013.01); *A61B 5/418* (2013.01); *A61B 8/485* (2013.01); *G01S 7/52022* (2013.01); *G01S 7/52036* (2013.01); *G01S 7/52042* (2013.01); *G01S 15/102* (2013.01)

(58) Field of Classification Search
CPC .......... A61B 5/415; A61B 5/418; A61B 8/00; A61B 8/485; G01S 7/52022; G01S 7/52036; G01S 7/52042; G01S 15/102
See application file for complete search history.

(56) References Cited

U.S. PATENT DOCUMENTS

| | | | |
|---|---|---|---|
| 5,810,731 | A | 9/1998 | Sarvazyan et al. |
| 5,921,928 | A | 7/1999 | Greenleaf et al. |

(Continued)

FOREIGN PATENT DOCUMENTS

| | | |
|---|---|---|
| CN | 1571649 A | 1/2005 |
| JP | 6483248 A | 3/1989 |

(Continued)

OTHER PUBLICATIONS

Brian J Fahey, Kathryn R Nightingale, Rendon C Nelson, Mark L Palmeri and Gregg E Trahey; "Acoustic radiation force impulse imaging of the abdomen:demonstration of feasibility and utility"; Ultrasound in medicine & biology ISSN 0301-5629 CODEN USMBA3; 2005, vol. 31, No. 9, pp. 1185-1198 [14 page(s) (article)].

(Continued)

*Primary Examiner* — Bo J Peng
(74) *Attorney, Agent, or Firm* — Seema S. Katragadda

(57) ABSTRACT

An ultrasound imaging method for detecting a target region of altered stiffness is provided. The method comprises delivering at least one reference pulse to the target region to detect an initial position of the target region, delivering a first pushing pulse having a first value of a variable parameter to a target region to displace the target region to a first displaced position, delivering a first tracking pulse to detect the first displaced position of the target region, delivering a second pushing pulse having a second value of the variable parameter to the target region to displace the target region to a second displaced position, and delivering a second tracking pulse to detect the second displaced position of the target region. An ultrasound imaging system for detecting a region of altered stiffness is also provided.

17 Claims, 15 Drawing Sheets

(56) References Cited

U.S. PATENT DOCUMENTS

| | | |
|---|---|---|
| 6,758,815 B2 | 7/2004 | Bernardi |
| 6,764,448 B2 | 7/2004 | Trahey et al. |
| 6,875,176 B2 | 4/2005 | Mourad et al. |
| 6,951,544 B2 | 10/2005 | Trahey et al. |
| 7,022,077 B2 | 4/2006 | Mourad et al. |
| 7,374,538 B2 * | 5/2008 | Nightingale et al. ......... 600/443 |
| 2003/0204141 A1 * | 10/2003 | Nock et al. .................... 600/439 |
| 2004/0167403 A1 * | 8/2004 | Nightingale et al. ......... 600/437 |
| 2005/0065426 A1 | 3/2005 | Porat et al. |
| 2005/0215899 A1 * | 9/2005 | Trahey et al. ................. 600/439 |
| 2006/0079773 A1 | 4/2006 | Mourad et al. |
| 2007/0197915 A1 | 8/2007 | Jeong et al. |
| 2009/0149753 A1 | 6/2009 | Govari et al. |
| 2009/0149760 A1 | 6/2009 | Bercoff et al. |

FOREIGN PATENT DOCUMENTS

| | | |
|---|---|---|
| JP | 2005532097 A | 10/2005 |
| JP | 2006034342 A | 2/2006 |
| JP | 2006305160 A | 11/2006 |
| JP | 2007195984 A | 8/2007 |
| JP | 2009142653 A | 7/2009 |

OTHER PUBLICATIONS

Kathryn Nightingale, Mark Palmeri, Richard Bouchard and Gregg Trahey; "Acoustic Radiation Force Impulse Imaging:A Parametric Analysis of Factors Affecting Image Quality"; 2003 IEEE Ultrasonics Symposium—549; 6pages.

Unofficial English translation of Japanese Office Action issued in connection with corresponding JP Application No. 2009-207668 on Apr. 1, 2014, 3 Pages.

Unofficial English translation of Office Action from CN dated Jul. 9, 2013, 7 Pages.

Unofficial English translation of Office Action issued in connection with corresponding JP Application No. 2009-207668 on Oct. 22, 2013, 5 Pages.

* cited by examiner

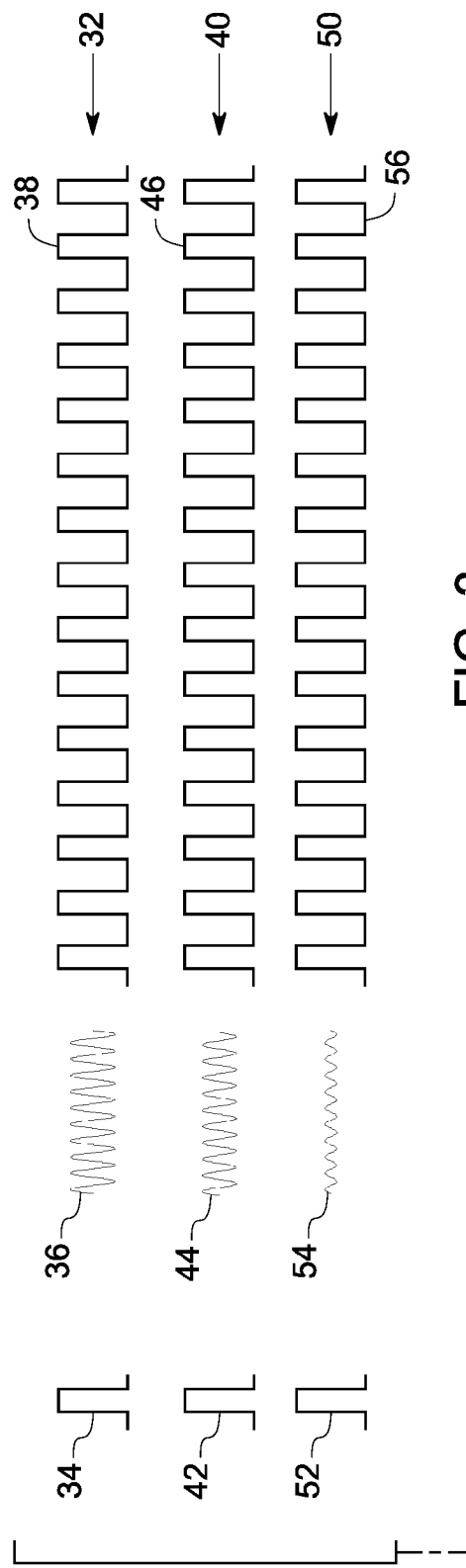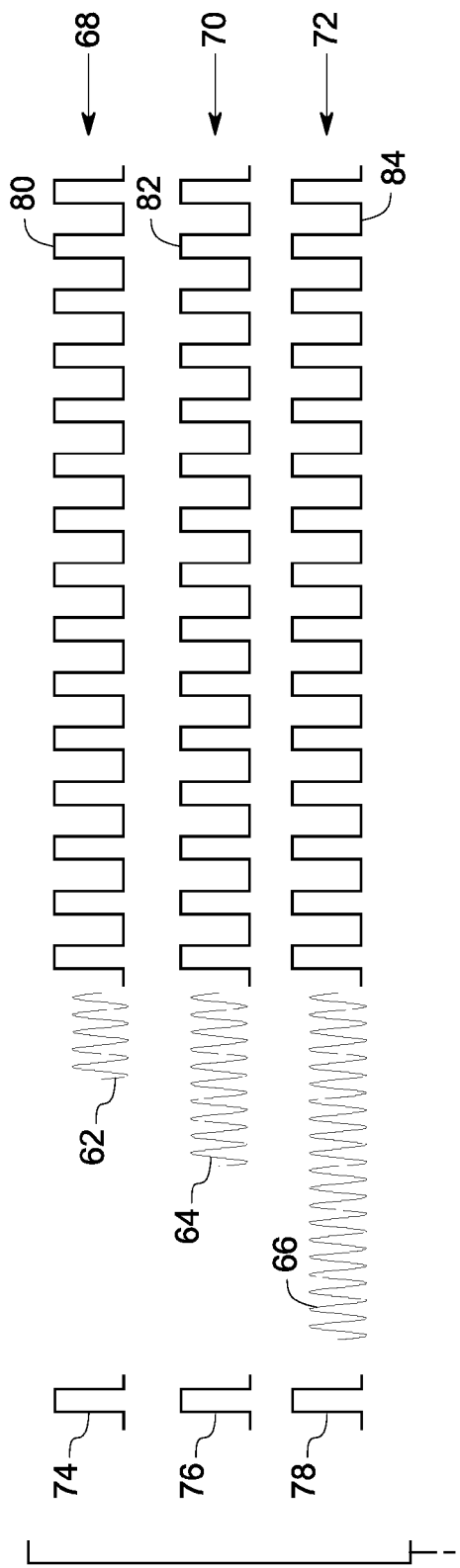

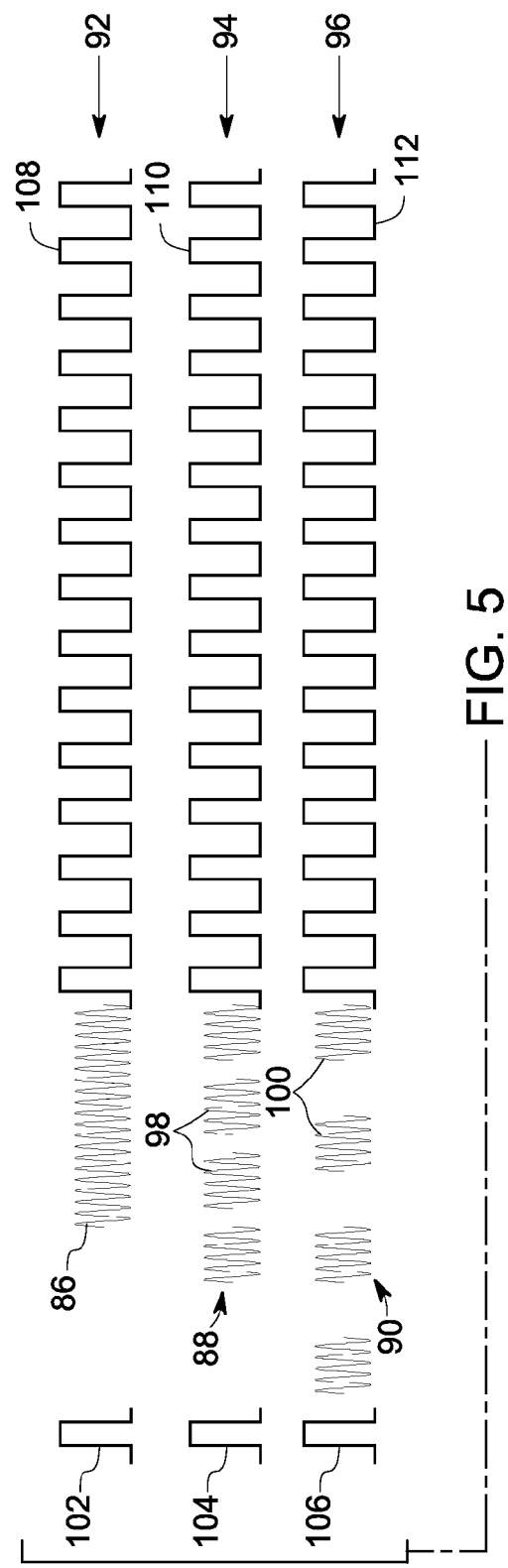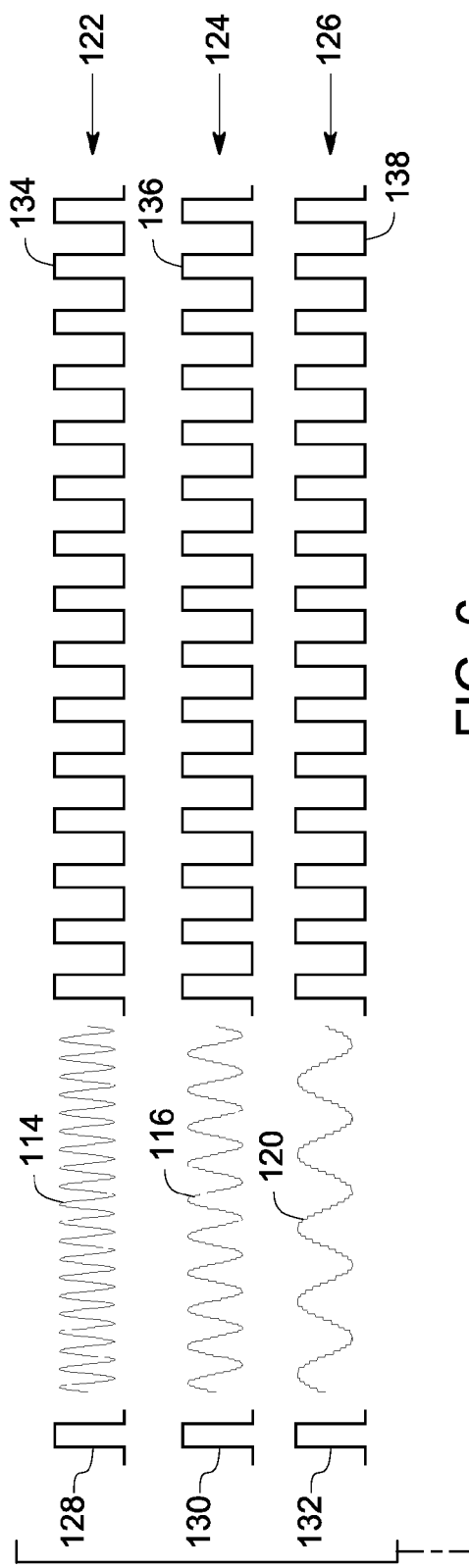

SYSTEMS AND METHODS FOR DETECTING REGIONS OF ALTERED STIFFNESS

BACKGROUND

Embodiments of the invention relate to ultrasound imaging, and more particularly to non-invasive methods for detecting regions of altered stiffness.

Tissue stiffness is a known marker of disease. For example, some cancerous tissues are stiffer than the normal surrounding tissues. Treatments for certain conditions, such as ablation, also create stiffer regions of tissue. Significant change in tissue stiffness can occur without a related change in ultrasound echogenicity. Quantitative measurements of stiffness would be useful clinically in the diagnosis of fibrosis and steatosis to identify fibrous liver, for example. Further, detecting stiffness can also help in finding tumors, some of which are not visible in conventional ultrasound imaging.

For these reasons, it is clinically useful to have a way of visualizing the stiffness of tissue. There are numerous methods for making such images using ultrasound. Most of these methods involve moving the tissue and tracking the motion or displacement of the tissue. In one method, the tissue is compressed by the sonographer pushing with the ultrasound probe, and the elastic response of the tissue is measured. In another method, tissue motion is created by vibrating the tissue at a low frequency with an external shaker. In other methods, radiation force is employed to move the tissue. Acoustic radiation force impulse (ARFI) ultrasound imaging is being used to detect areas having altered stiffness. The basic idea of ARFI is to push the tissue with acoustic radiation and then use tracking techniques to detect the motion caused by the acoustic radiation.

It is known that, the stress-strain or equivalently the force-displacement relationship for healthy and diseased tissues are generally non-linear. The non-linear response of the tissue may provide additional information about the tissue that could improve the detection of cancer or other clinical conditions. For example, invasive ductal carcinoma (IDC) and normal glandular breast tissue have very different non-linear stress-strain relationships. The IDC becomes increasingly stiffer as the applied force is increased. The healthy glandular tissue also becomes stiffer as the applied force increases, but the slope of the curve for IDC is much steeper.

BRIEF DESCRIPTION

In one embodiment, an ultrasound imaging method for detecting a target region of altered stiffness is provided. The method comprises delivering at least one reference pulse to the target region to detect an initial position of the target region, delivering a first pushing pulse having a first value of a variable parameter to a target region to displace the target region to a first displaced position, delivering a first tracking pulse to detect the first displaced position of the target region, delivering a second pushing pulse having a second value of the variable parameter to the target region to displace the target region to a second displaced position, and delivering a second tracking pulse to detect the second displaced position of the target region.

In another embodiment, a method of detecting a target region of altered stiffness is provided. The method includes delivering pushing pulses at a target region while varying a variable parameter of the pushing pulses, and tracking displacements in one or more regions disposed outside the target region.

In yet another embodiment, a method of detecting areas of altered stiffness is provided. The method comprises delivering two or more pulse sequences to a target region, where each of the two or more pulse sequences comprises a pushing pulse and a tracking pulse, and where a variable parameter of the pulse sequence is varied between the two or more pulse sequences. The method further comprises mapping a displacement of the target region with respect to the variable parameter to detect the region of altered stiffness.

In another embodiment, an ultrasound imaging system for detecting a region of altered stiffness is provided. The system comprises a transducer array configured to deliver two or more pulse sequences to a target region, where the pulse sequence comprises a tracking pulse and a pushing pulse, and where a variable parameter of the pushing pulse is varied between the two or more pulse sequences. The system further comprises a controller for controlling the two or more pulse sequences being delivered to the target regions, and a signal processing unit for processing received data from the target region in response to the two or more pulse sequences.

DRAWINGS

These and other features, aspects, and advantages of the present invention will become better understood when the following detailed description is read with reference to the accompanying drawings in which like characters represent like parts throughout the drawings, wherein:

FIGS. 3-8 are schematic representations of pulse sequences that are delivered to target regions, in accordance with embodiments of the present technique;

DETAILED DESCRIPTION

Figure 1:
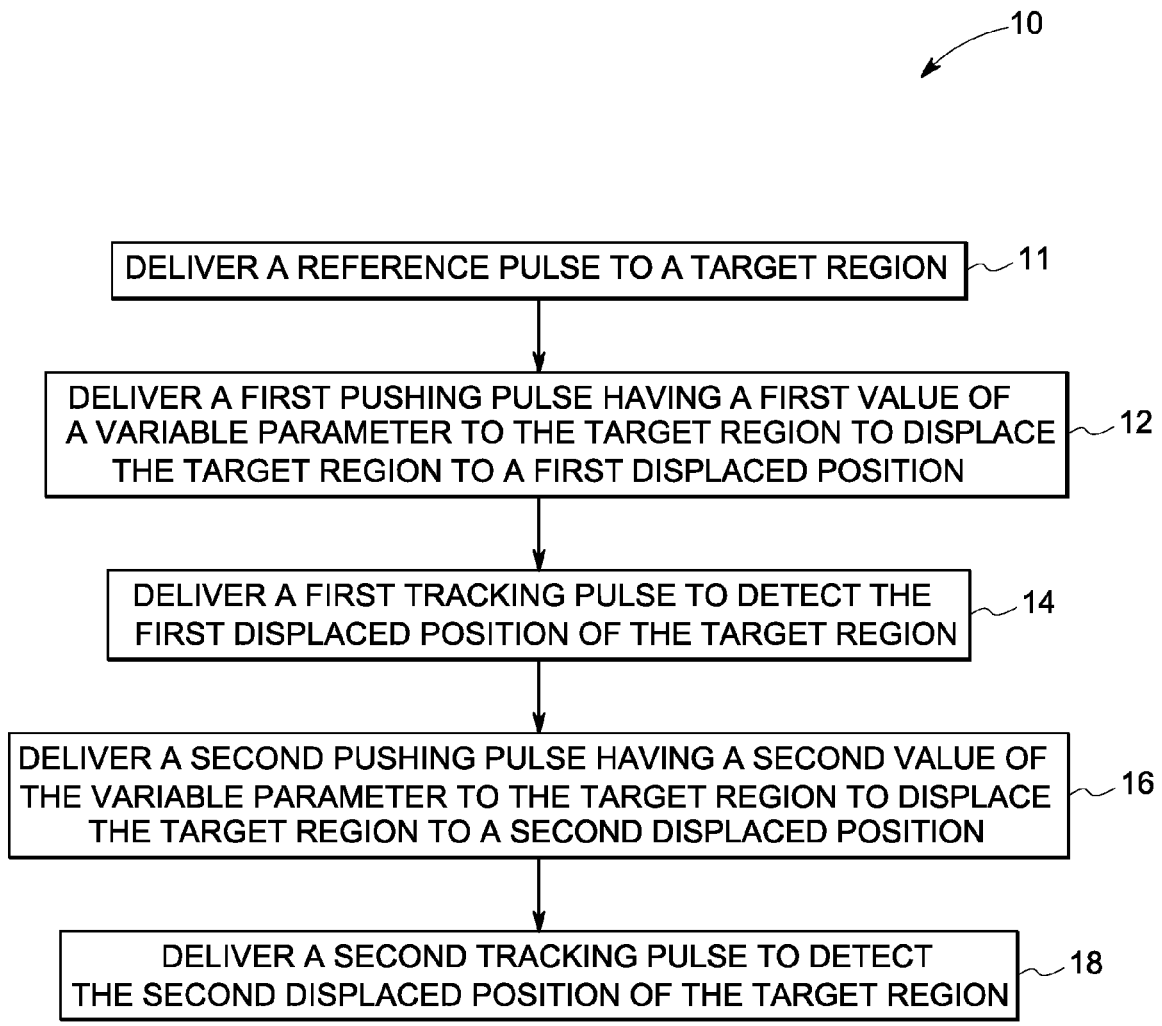
FIG. 1 is a flow chart for an ultrasound imaging method used for detecting a region of altered stiffness, in accordance with embodiments of the present technique; illustrating the sequence of delivering pushing and tracking pulses in the target region.

Tissue stiffness is a known marker of diseases. Measuring the stiffness of tissues using non-invasive diagnostic methods provides one with the opportunity of detecting onset of a disease or the existence of a disease. As used herein, the term "stiffness" refers to resistance of an elastic body to deflection or deformation by an applied force. For example, an area of relatively higher stiffness may be a warning sign of cancer. In another example, when cancerous tumors form on an organ, such as the liver, at least a portion of the affected organ becomes stiffer than surrounding tissues. Normal glandular tissues and fibrous tissues, as well as ductal and intraductal tumors exhibit non-linear characteristics. If a material or tissue exhibits a non-linear stress-strain relationship that means that the elastic moduli of the tissues vary with the applied compression. The shape of the stress-strain curve may be different for different tissues, which provides a source of contrast and tissue discrimination. Healthy tissue may exhibit a different stress-strain relationship than diseased tissue, so determining information about the stress-strain curve may enable one to discover disease.

Acoustic radiation force impulse imaging is one technique used to make images representative of the stiffness of tissues. As will be appreciated, a basic ARFI pulse sequence allows displacements caused by the pushing pulse to be determined as a function of space and time. In the ARFI pulse sequence, a reference pulse is delivered or fired at a target region to determine the position of the target region prior to disturbance. Subsequently, a pushing pulse is delivered to displace the target region, followed by a tracking pulse, or series of tracking pulses, to determine the displacement of the target region. The displacement of the target region is then mapped to determine the region having varying stiffness.

Embodiments of the present technique are directed to detecting regions of altered stiffness using ultrasound imaging. The present technique may be used for either diagnostic or prognostic purposes. Also, the ultrasound imaging may be two-dimensional or a three-dimensional imaging. As used herein, the term "regions of altered stiffness" refers to regions of increased or decreased stiffness relative to the average surrounding tissue. For example, the regions of altered stiffness may include tumors, cancerous tissues, ablated tissues (in case of ablation treatment), a hardened blood vessel, muscle tissue with greater muscle tone relative to other regions, a region of lesser stiffness relative to other regions indicated by a region of greater displacement within the image.

In certain embodiments, an ultrasound imaging method for detecting a region of altered stiffness comprises delivering a reference pulse to a target region to determine a reference position of the target region, then firing a first pushing pulse having a first value of a variable parameter to the target region to displace the target region to a first displaced position, delivering a subsequent tracking pulse to detect the first displaced position of the target region, delivering a second pushing pulse having a second value of the variable parameter to the target region to displace the target region to a second displaced position, and delivering a second tracking pulse, or a series of tracking pulses, to detect the second displaced position of the target region. As used herein, the term "target region" encompasses one or more elastic regions. As used herein, the term "tracking pulse" may either employ a single pulse, or a series of pulses. In one embodiment, the target region may include biological tissues. For example, the target region may include liver tissues, breast tissues, prostate tissues, thyroid tissues, lymph nodes, vascular structures, kidney, etc.

In certain embodiments, a displacement of the target region as a result of exposure to pushing pulses with variable parameters is detected. The tracking pulses may be delivered to the target region to evaluate the change in the displacement of the target region as a result of delivering the pushing pulses. In one embodiment, the displacement of the target region may be monitored while the force is being applied by the pushing pulse. For example, the displacement may be monitored by interspersing the pushing pulses and the tracking pulses. Whereas, in another embodiment, the displacement of the target region may be monitored after cessation of the pushing pulses. In this embodiment, the tracking pulse, or series of tracking pulses, may be delivered after delivering the pushing pulses.

In certain embodiments of the present technique, the pulse sequence may be repeated while varying one or more variable parameters of the pushing pulse. In these embodiments, non-linear responses of the target region are mapped to the variable parameters of the pushing pulses. These non-linear responses are then used to discriminate between different types of tissues. As will be described in detail below, in the present technique, mapping the displacement response of the target region with respect to variable parameters of the pushing pulse enables enhanced tissue discrimination.

Turning now to FIG. 1, a flow chart 10 illustrating a method of delivering a pulse sequence in an ultrasound imaging method used for detecting a region of altered stiffness is shown. The delivery of the pulse sequence includes delivering reference, pushing and tracking pulses in the target region. In the illustrated embodiment, a reference pulse is used to determine a reference or initial position of the undisturbed tissue (block 11), and a first pushing pulse having a first value of a variable parameter is delivered to a target region to displace the target region to a first displaced position (block 12).

Next, after sufficient time has passed such that the motion induced by the first pushing pulse decreases to determined levels; a first tracking pulse or tracking pulse sequence is delivered to detect the first displaced position of the target region (block 14). Alternatively, the first displaced position of the target region may be detected by interspersing the first pushing pulse with the first tracking pulse. Using a series of tracking pulses enables monitoring the displacements of the tissue as a function of time.

Although not illustrated, in one embodiment, an additional reference pulse may be delivered to the tissue prior to delivering the second pushing pulse to determine if the position of tissue has returned to a resting state and/or to provide a new reference position for the tissue.

At block 16, a second pushing pulse having a second value of the variable parameter is delivered to the target region to displace the target region to a second displaced position. In one embodiment, the second pushing pulse may be delivered after the motion induced by the first pushing pulse is reduced to a determined value. Next, another tracking pulse, or series of tracking pulses, is delivered to detect the second displaced position of the target region (block 18). The displacements of the target region resulting from change in value of the variable parameter are then mapped with respect to the variable parameter.

When a pushing pulse with a particular value of one of the variable parameters (pulse length for example) is delivered the pushing pulse imposes a radiation force capable of displacing the tissue. This radiation force varies by changing the variable parameters. This results in a different displacement, which depends on two features, the force applied, and the tissue to which the force is being applied.

In certain embodiments, various parameters of the pushing pulses may be varied as described in the following non-limiting examples. In one embodiment, the length of the pushing pulse or the length of the pushing pulse packet may be changed. For a packet pushing pulse, the pulse repetition frequency (PRF) of the pushing packet may be varied. In other words, the duty cycle of the pushing pulse may be varied. As used herein, the term "Pulse Repetition Frequency (PRF)" refers to the number of pulses transmitted per second by the transducer array. In another embodiment, the frequency of the pushing pulse may be varied. As will be appreciated, acoustic radiation force is proportional to the absorption coefficient of the tissue and the absorption coefficient is a function of frequency. Changing the frequency of the pushing pulse changes the amount of energy absorbed by the tissue, and thus changes the applied force. In another embodiment, the waveform of the pushing pulse may be designed to optimize the radiation force for a given application. These designs could include non-linear propagation effects. For example, by accounting for the non-linear propagation effects, the pulse sequences may be made to apply force at the desired depths. In yet another embodiment, the variable parameter of the pushing pulse comprises amplitude, a peak power, an average power, a length, a frequency, a waveform, or combinations thereof. As will be discussed in detail below, in certain embodiments, more than one variable parameter of the pushing pulse may be varied to detect a region with altered stiffness. For example, amplitude of the pushing pulse may be varied, and the displacement of the target region may be mapped with respect to the change in value of the amplitude. Subsequently, a pulse length of the pushing pulse may be varied, and the displacement of the target region may be mapped with respect to the change in value of the pulse length.

The pulse repetition frequency (PRF) of the tracking pulses determines the sampling frequency of the displacement data. Using a series of tracking pulses provides data, which allows one to calculate parameters as a function of time. For example, the data can be used to allow one to calculate the maximum displacement over time, the time it takes for the tissue to relax back to its original position, the derivative of this displacement (velocity), and other displacement related parameters. This data along with the reference data may be used to filter out undesired tissue motion.

The procedure of blocks 12-18 may be repeated for each value of the parameter being varied (for example, for all the different pulse lengths). Subsequently, by using the data a series of displacements over time may be generated for each pushing location and value of variable parameter. These displacements are mapped to determine non-linear behaviors of the tissues.

In all embodiments, before delivering the pushing pulses and tracking pulses, a reference pulse may be delivered to the target region to detect the initial un-displaced position of the target region. In this embodiment, the displacement position of the target region may then be calculated by comparing the initial position with the first displaced position as detected by the first tracking pulse. The reference pulse is delivered or fired in a direction of interest. The reference pulse may be a standard ultrasound pulse typically used in B-mode or Color Doppler imaging. As used herein, the term "standard ultrasound pulse" indicates that the length and amplitude of the pulse is similar to that used in making a B-mode or Color Doppler image. These standard pulses are of much lower amplitude and shorter length than the pushing pulses employed in the present technique. The reference pulse may be chosen based on the desired outcome. For example, longer pulses may be used for robust displacement measurement. Whereas, short pulses may be used if axial resolution is required.

In certain embodiments, more than one target region may be detected simultaneously. In these embodiments, the pushing pulses and the tracking pulses may be delivered at these target regions simultaneously. The techniques used to create images with a larger region of interest with fewer transmit events apply here as they do in more standard imaging techniques. These include multi-line transmit in which more than one beam is created for a single or group of transmits. This is done by either transmitting a wide beam that is configured to excite a larger area, or transmit to multiple regions simultaneously, or by transmitted to multiple regions in quick succession.

Figure 2:
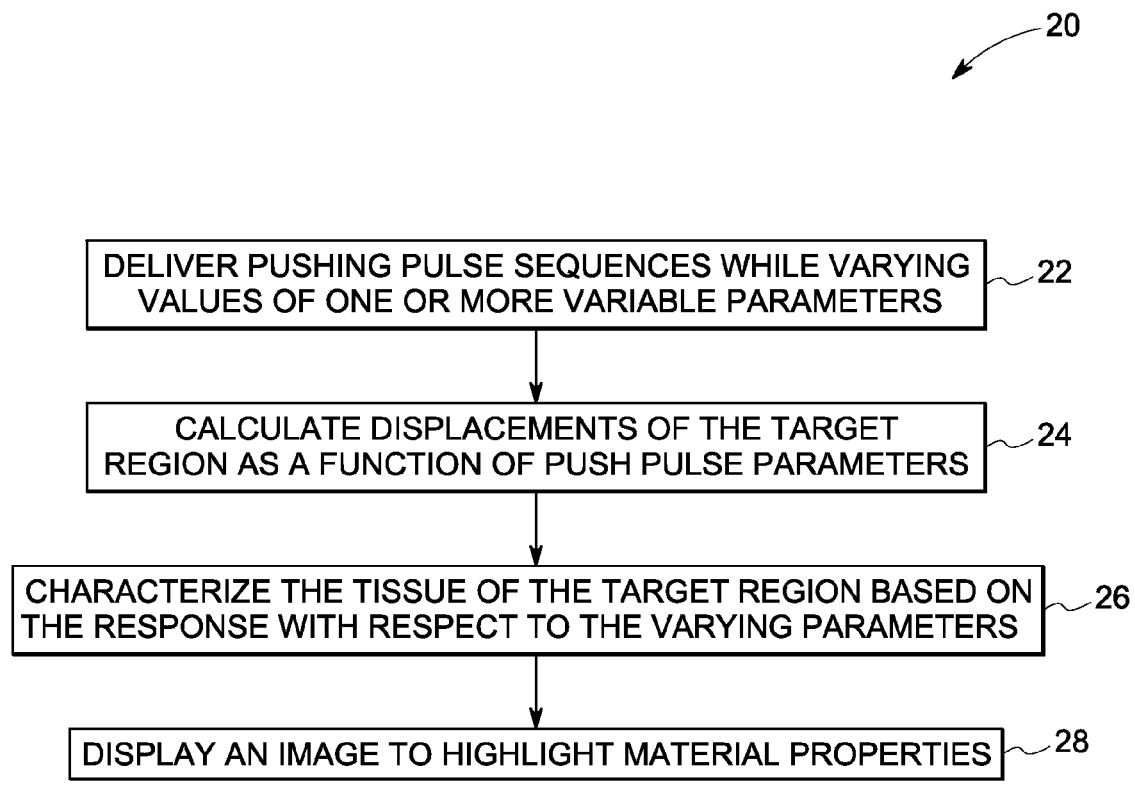
FIG. 2 is a flow chart for displaying an image of a target region having altered stiffness, in accordance with embodiments of the present technique.
Figure 18:
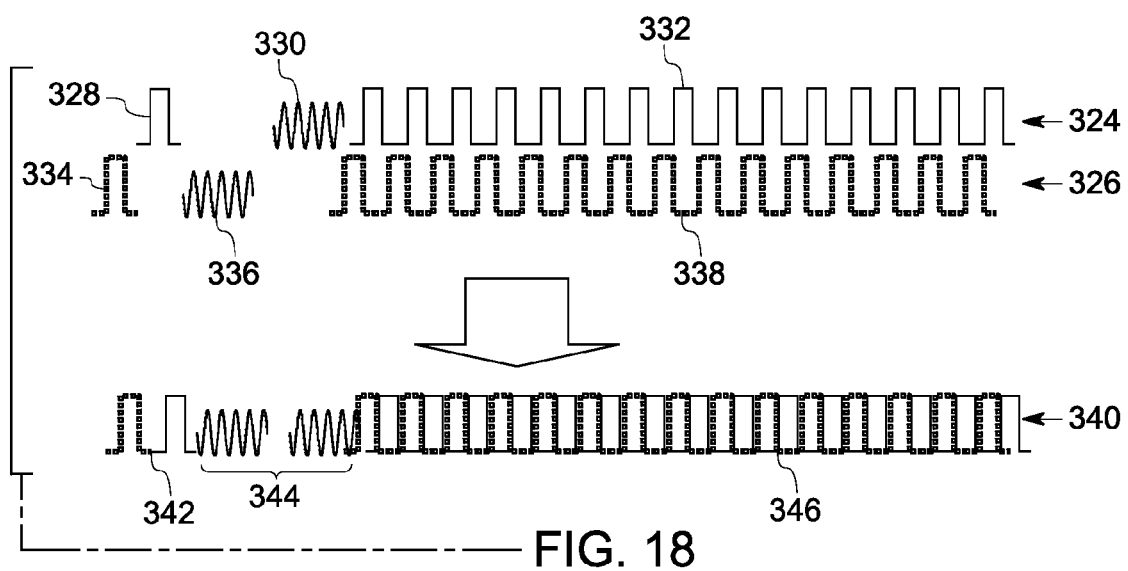
FIG. 18 are drawings for interleaving of pulse sequences, in accordance with embodiments of the present technique.

FIG. 2 illustrates a flow chart 20 for displaying an image of a target region having altered stiffness. In accordance with the illustrated embodiment, in order to map the non-linear response of the tissues, the parameters of the pushing pulse are varied. At block 22, pulse sequences having pushing pulses with different values of one or more variable parameters are delivered. In one embodiment, pushing pulses with one variable parameter may be delivered at a first target region while gradually varying the value of the variable parameters of the pushing pulses from an initial value to a determined value, before moving to a second target region. In another embodiment, pushing pulses with the same value of the variable parameter may be delivered to the different target regions. Subsequently, the value of the variable parameter of the pushing pulses may be changed to the next value, and the pushing pulses with the next value of the variable parameter may then be delivered to the target regions. The techniques described herein require delivering multiple pulses to each location, including pushing and tracking pulses. As will be appreciated, in standard color flow imaging multiple pulses are delivered to the same location to determine the velocity of a target. In embodiments of the present technique, interleaving may be employed in a way similar to its use in color flow imaging. As used herein, the term "interleaving" encompasses a process of successively delivering a plurality of pulses to multiple target regions, and subsequently changing at least one variable parameter of the pushing pulses and delivering the changed pushing pulses for the same set of target regions. In certain embodiments, the interleaving process may be applied for the non-linear displacement mapping pulses described herein. Interleaving may be advantageous in the present technique because tissue heating may occur if the large and long push pulses are repeatedly applied to the same location. This process of changing the value of the variable parameter and delivering the pushing pulses with the changed variable parameter may be continued for all the determined subsequent values of the variable parameter. In one embodiment, interleaving may include breaking a pushing pulse into a plurality of pulses, and delivering tracking pulses between the plurality of pulses, thereby allowing the user to observe the displacement of the target region while pushing the target region. As described in more detail in FIG. 18, in another embodiment, interleaving may include delivering pulse sequences at other locations in the time gap where the tracking and pushing pulses are not being delivered to a first location. Typically, the time gap between the delivering of the pulse sequences to a particular target region is either wasted or used to cool the ultrasound probe or tissue, however, this time gap may be used to deliver the pulse sequences at locations other than the particular target region. In yet another embodiment, interleaving includes delivering pulse sequences at a single target region while varying the variable parameter, and subsequently moving to a next target region, or delivering a pulse sequence having a particular value of the variable parameter to all the target regions, before changing the variable parameter to the next value and again delivering the pulse sequences with the second value of the variable parameter to all the target regions.

As will be described in detail with respect to FIGS. 3-8, in one embodiment, the amplitude of the pushing pulse may be varied. As used herein, the term "amplitude" encompasses the peak pressure, or the root-mean-square (RMS) pressure, or the peak or RMS voltage or current applied to the transducer, or the peak or average power delivered.

At block 24, the data is collected and the displacement of each of the target regions is separately mapped with respect to the variable parameter. It should be noted that in addition to the non-linear behavior of certain tissues, the imaging system itself may respond in a non-linear fashion. Therefore, all the non-linear behavior may not directly be attributable to the tissue. These system non-linearities need to be characterized in order to properly interpret the collected data. For example, the output of the transducer may not be directly proportional to the input electrical signal. In this case, changing the amplitude of the electrical excitation may not lead to a linear change in the transmitted waveform. If this non-proportional response of the output of the transducer is not accounted for it may be misinterpreted as non-linearity in the tissue or material.

At block 26, the tissues of the target regions are characterized based on the response with respect to the varying parameter(s). Additionally, pushing pulses with a varying value of another pushing pulse parameter may also be delivered to the target regions and the displacement of the target regions may be mapped with respect to the one or more pushing pulse parameters to increase the information about the material properties of the tissues being imaged. For example, it may be useful to excite the tissue with different amplitude and at different pushing pulse repetition frequencies to obtain information about the non-linear response of the tissue as a function of frequency. In one example, both the amplitude and PRF were varied for the pushing pulses. At block 28, an image of the scanned target region is created using the data acquired. As will be appreciated, a scalar value for each location that represents the data is required to make an image. This may be done by creating a function that takes the data as an input and has a scalar output for each location. For example, the displacements may be fit using a mathematical model and an image of a model parameter may be created. In one embodiment, the displacements of the target regions are the input, the model fit is the function, and the output, which is displayed is the model parameter.

FIGS. 3-8 illustrate different pulse sequences that may be delivered to the one or more target regions to obtain information on the tissues of the target regions. Specific embodiments discussed in FIGS. 3-8 are merely exemplary embodiments of the pulse sequences and do not limit the scope of the present technique Further, the illustrated pulse sequences may be delivered to a single target region. Alternatively, the pulse sequences may be delivered to two or more target regions.

Referring now to FIG. 3, each of the pulse sequences 32, 40 and 50 include a reference pulse, tracking pulses and pushing pulses. While the characteristics, such as amplitude, frequency, and the like of the reference pulses 34, 42 and 52 and the tracking pulses 38, 46 and 56 are held constant in the three sequences 32, 40 and 50, respectively, the amplitude of the pushing pulses 36, 44 and 54 is gradually decreased from the sequence 32 to 50. In the illustrated embodiment, the sequences 32, 40 and 50 may be delivered at one or more target regions. In the presently contemplated embodiment, the displacement of the target regions is calculated as a function of the pushing pulse amplitude.

In the illustrated embodiment of FIG. 4, the length of the pushing pulses 62, 64 and 66 of the pulse sequences 68, 70 and 72, respectively, are varied. As with the pulse sequences of FIG. 3, in the illustrated embodiment, the reference pulses 74, 76 and 78 and the tracking pulses 80, 82 and 84 of the sequences 68, 70 and 72, respectively, are held constant. The displacement of the target regions is calculated as a function of the length of the pushing pulses 62, 64 and 66.

Turning now to FIG. 5, the pulse repetition frequency (PRF) of the pushing pulses 86, 88 and 90 of the pulse sequences 92, 94 and 96, respectively, is varied. The pushing pulses 88 and 90 are delivered in the form of plurality of packets 98 and 100, respectively, with an interval as decided by the PRF. Each of the plurality of packets 98 and 100 include a plurality of pulses that together form pushing pulses 88 and 90, respectively. The reference pulses 102, 104 and 106 and the tracking pulses 108, 110 and 112 are held constant.

Another example of the variation in pushing pulses is illustrated in FIG. 6. In the illustrated embodiment, the frequency of the pushing pulses 114, 116 and 120 is varied between pulse sequences 122, 124 and 126, respectively. The reference pulses 128, 130 and 132 and the tracking pulses 134, 136 and 138 are held constant.

Figure 7:
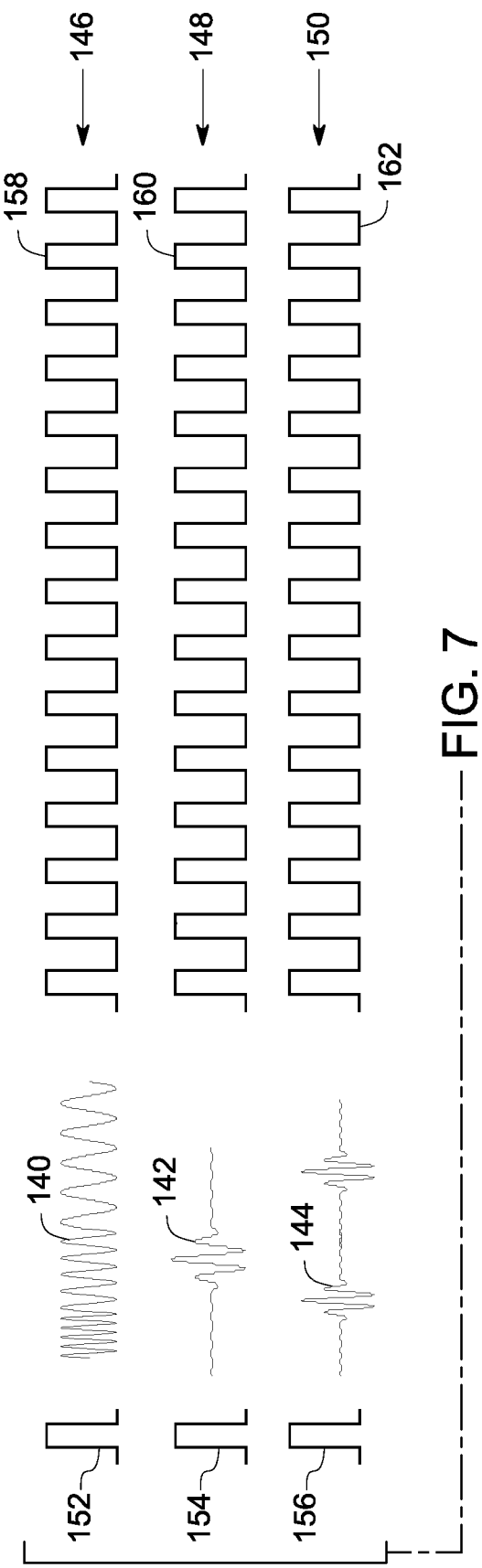

FIG. 7 illustrates an embodiment where waveforms of the pushing pulses 140, 142 and 144 are varied between the pulse sequences 146, 148 and 150, respectively. The reference pulses 152, 154 and 156 and the tracking pulses 158, 160 and 162 are held constant.

Figure 8:
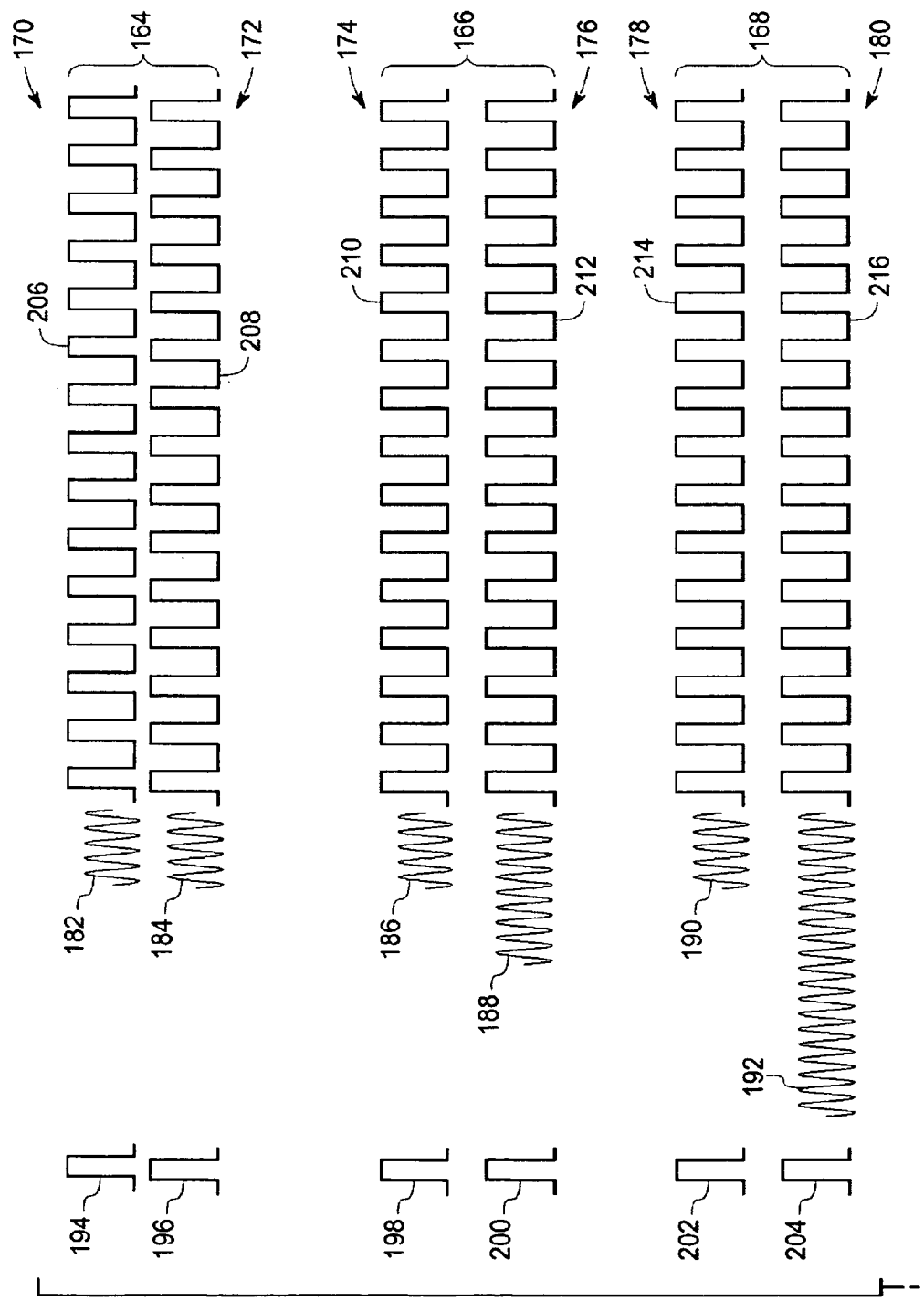
Figure 9:
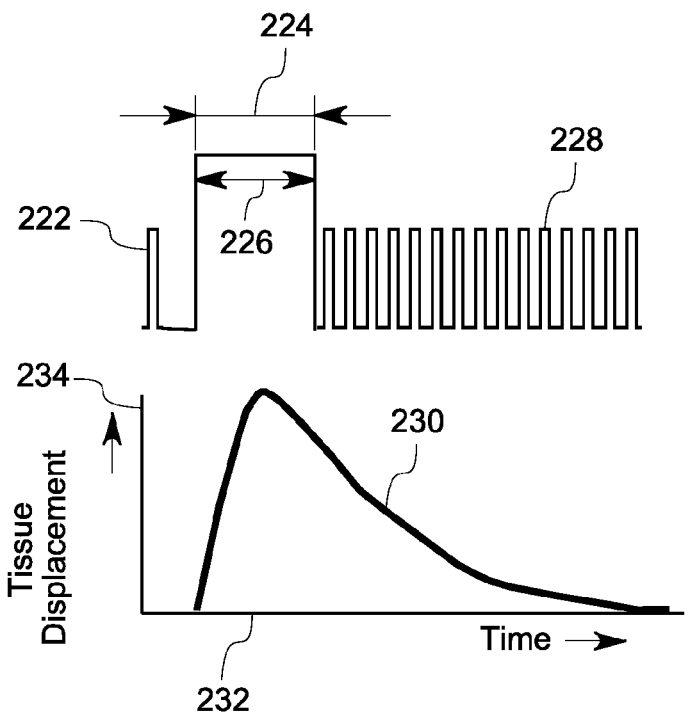
FIGS. 9-12 are schematic representations illustrating pulse sequences with varying pushing pulse parameters and the co-relation between the variable parameter of the pushing pulse and the displacement response of the tissues in the target region, in accordance with embodiments of the present technique.
Figure 10:
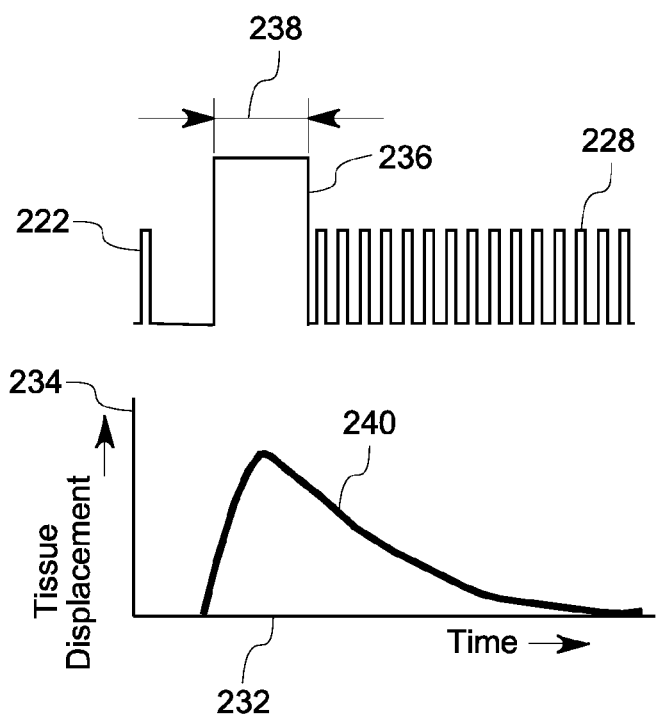
Figure 11:
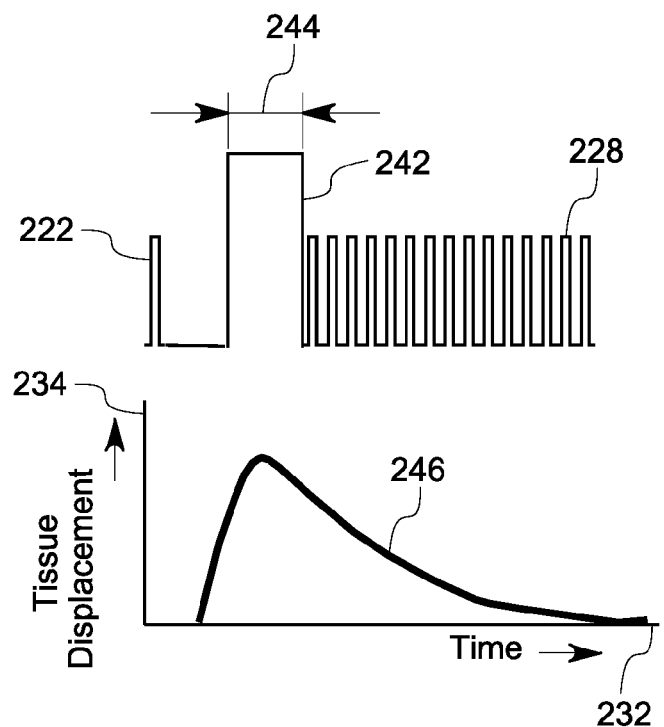
Figure 12:
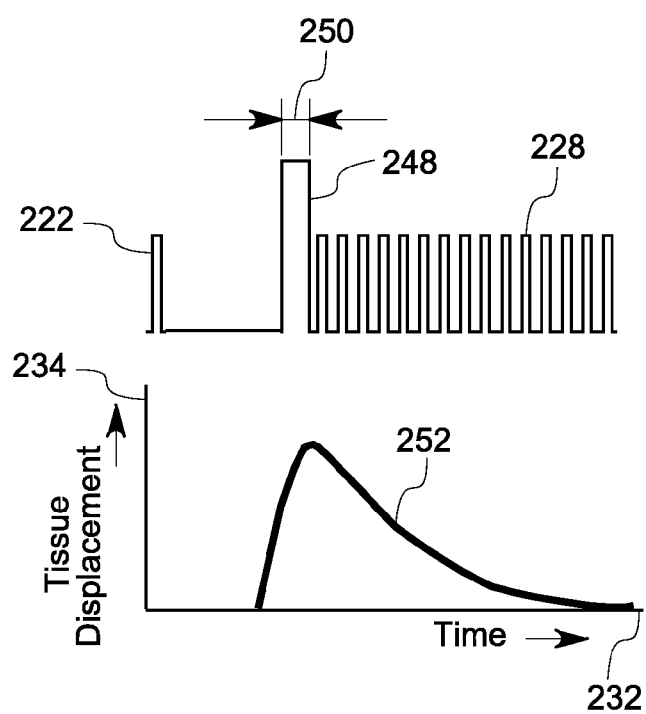

FIG. 8 illustrates a further enhancement of the scan sequence to improve performance in the presence of respiratory, cardiac, or other motion. Each pair includes at least two firing sequences. For example, the pair 164 includes firing sequences 170 and 172, the pair 166 includes firing sequences 174 and 176, and the pair 168 includes firing sequences 178, 180. In addition, each of the firing sequences 170, 172, 174, 176, 178, and 180 includes a corresponding reference pulse 194, 196, 198, 200, 202, 204, a corresponding pushing pulse 182, 184, 186, 188, 190, 192, and a corresponding tracking pulse 206, 208, 210, 212, 214, and 216, as depicted in FIG. 8. In this embodiment variable parameter values of the pushing pulses 182, 184, 186, 188, 190, and 192 are used as in the other embodiments. However, a particular value of the parameter being varied is chosen as a reference value and pairs of the variable parameter values are fired sequentially. One of the variable parameters of the pair is made the reference value and the value of the other variable parameter in the pair is varied. The displacements from the pairs are compared which gives the relative difference or ratio of displacements for the varied values referenced to the reference value of the parameter. In this way, if there is motion or slow changes, the impact is reduced because of the comparison made with a value delivered close in time. By repeating the same firing sequence in each pair, one can also normalize out other effects. For example, if a trend is observed in the reference it can be removed from the pair firings.

In the illustrated embodiment, the pulse sequence described is for a single location. However, in some embodiments, pulse sequence may also be repeated for two or more locations to form an image. The pulse sequence may be delivered to the two or more different locations in different ways as will be discussed below. Also, in these embodiments the pulse sequence may be varied depending on the application. In some embodiments, these variations may affect the quality and type of data that may be acquired.

FIGS. 9-12 illustrate displacement response of a target region with change in length of the pushing pulses. In the illustrated embodiment, an example pulse sequence employing pushing pulses with varying lengths is employed. In the illustrated embodiment, a ARFI scan sequence is repeated four times, however, unlike the conventional ARFI scan sequence, a pushing pulse parameter (length) is varied each time. In the illustrated embodiments, each time the length of the pushing pulse is decreased.

Referring now to FIGS. 9-12, FIG. 9 illustrates a pulse sequence having a reference pulse 222, a pushing pulse 226, and tracking pulses 228. The reference numeral 224 represents a length of the pushing pulse 226. The graph 230 represents the displacement of the target region. Abscissa 232 represents time, and the ordinate 234 represents the displacement of the target region. As the length of the pushing pulses is decreased gradually the peak displacement induced by these pushing pulses is reduced, as represented in graphs 240, 246 and 252, respectively. As illustrated, the pushing pulse 236 has a length 238, the pushing pulse 242 has a length 244, the pushing pulse 248 has a length 250. In the presently contemplated embodiment, the displacement of the target region is allowed to settle back to the resting displacement before the next pushing pulse is delivered.

Figure 13:
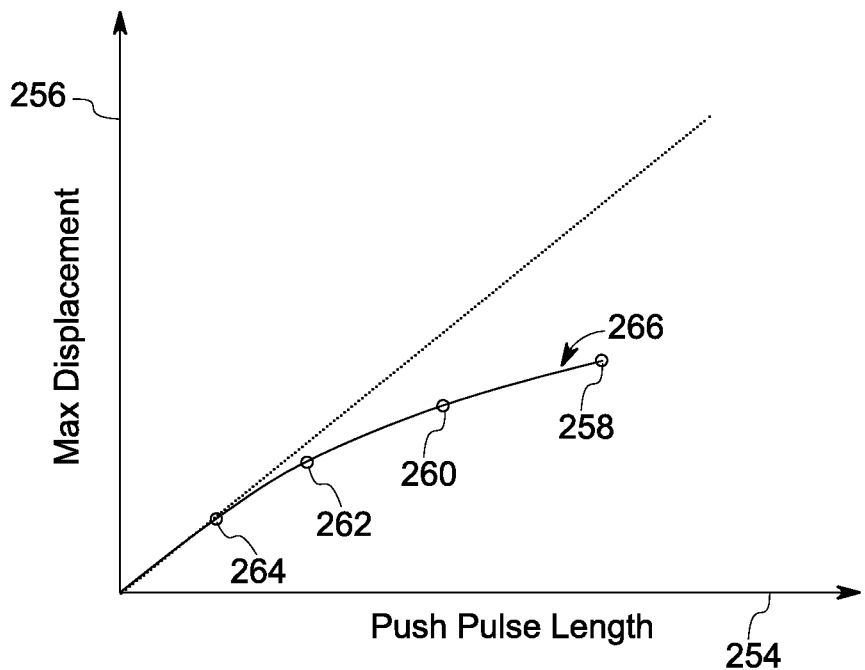
FIGS. 13-16 are graphical representations illustrating maximum displacement of linear and non-linear materials, in accordance with embodiments of the present technique.

FIG. 13 illustrates the displacement graph for the displacements of the target region with respect to the change in pushing pulse lengths of FIGS. 9-12. Abscissa 254 represents the length of the pushing pulse, and the ordinate 256 represents the maximum displacement of the target region. The points 258, 260, 262 and 264 on the curve 266 represent the displacements of the target regions upon application of pushing pulses of FIG. 9, FIG. 10, FIG. 11, and FIG. 12, respectively. In the illustrated embodiment, the displacement of the target region is taken as the maximum displacement or peak of the displacement curves from FIGS. 9-12. As illustrated by the curve 266, the material is showing a non-linear response. For small pushing pulse lengths or small displacements there is a linear response initially. However, as the pulse length is increased the maximum displacements are smaller than the linear extrapolation from earlier data points. In other words, the material becomes "stiffer" as it is pushed more and more by the acoustic pulses. This phenomenon is sometimes referred to as strain hardening. The shape of this curve in someway characterizes the material, or at least provides a possible source of contrast from other materials.

Figure 14:
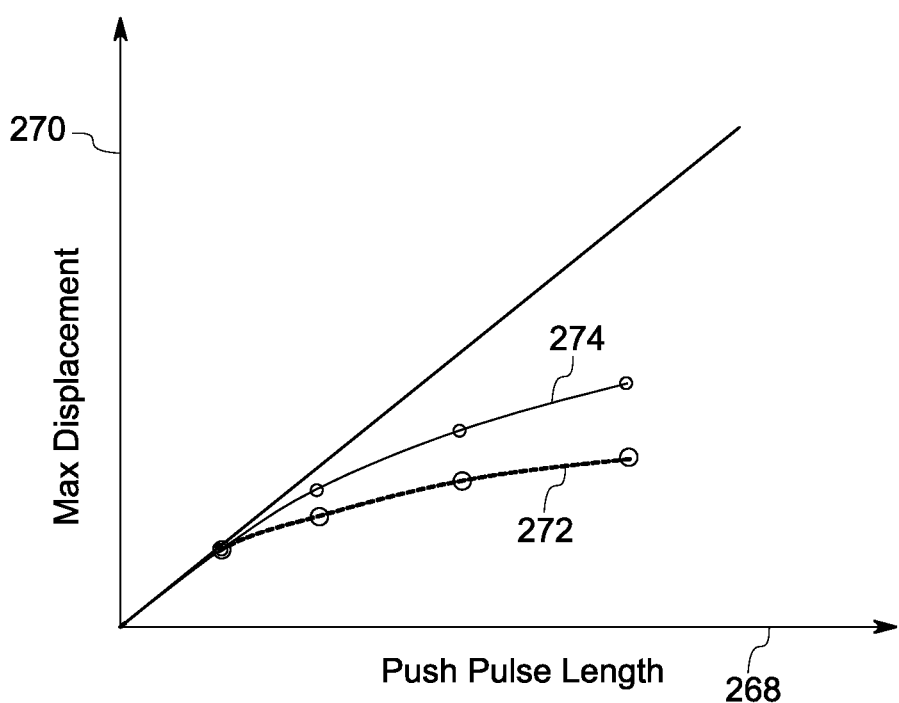

FIG. 14 shows the displacement response of target regions having two different material characteristics. Abscissa 268 represents the length of the pushing pulse, and the ordinate 270 represents the maximum displacement of the target region for four pulse sequences delivered one at a time with the pushing pulse length being varied for each pulse sequence. Graph 272 represents the response of a first material, and graph 274 represents the response of the second material to the pulse sequences. As illustrated by graphs 272 and 274, each of the materials exhibit a different non-linear response to the varied pushing pulse lengths. Although, initially both first and second materials have a similar displacement for low pushing pulse lengths. However, with the increase in the length of the pushing pulses the two materials act in a non-linear fashion and produce smaller displacements than the linear extrapolation of the low pushing pulse length data. The two curves 272 and 274 may be used to discriminate between the two materials.

Figure 15:
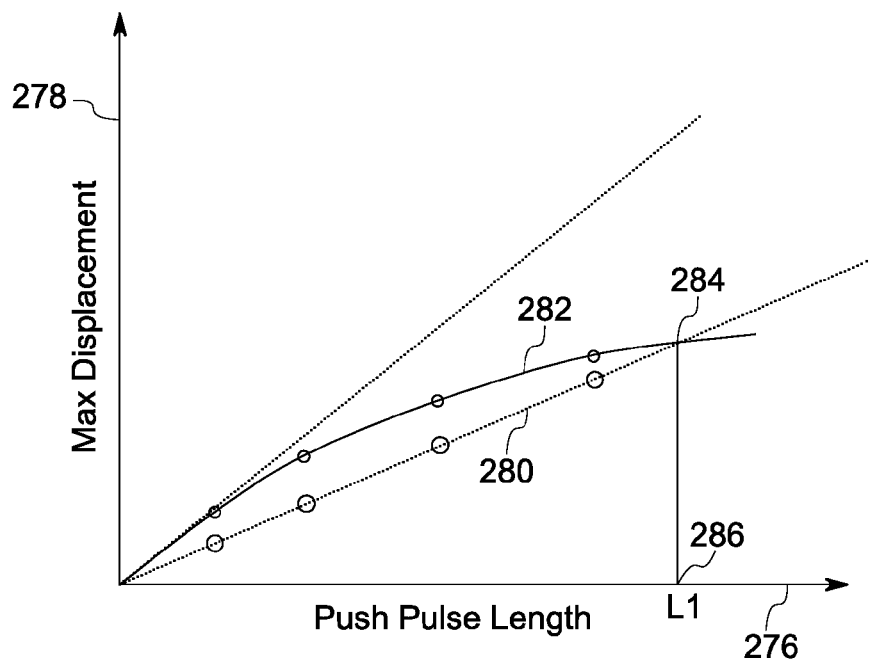

FIG. 15 shows response curve 280 for a material that exhibits a linear response in displacement with the change in the length of the pushing pulse, whereas the response curve 282 shows a non-linear response of another material. Abscissa 276 represents the length of the pushing pulse, and the ordinate 278 represents the maximum displacement of the target region for four pulse sequences delivered one at a time with the pushing pulse length being varied for each pulse sequence. As will be appreciated, typically linear materials exhibit different slopes in the line of displacement versus length of the pushing pulse. However, as represented by the point 284, the linear and non-linear materials have similar displacements at a given pushing pulse length L1, represented by the reference numeral 286. Therefore, if the displacement response is taken at the pushing pulse length L1, than the linear and non-linear materials may be incorrectly identified as the same material. Whereas, by taking the displacement response of the two materials at varying lengths of the pushing pulse, the two materials are identified correctly.

Figure 16:
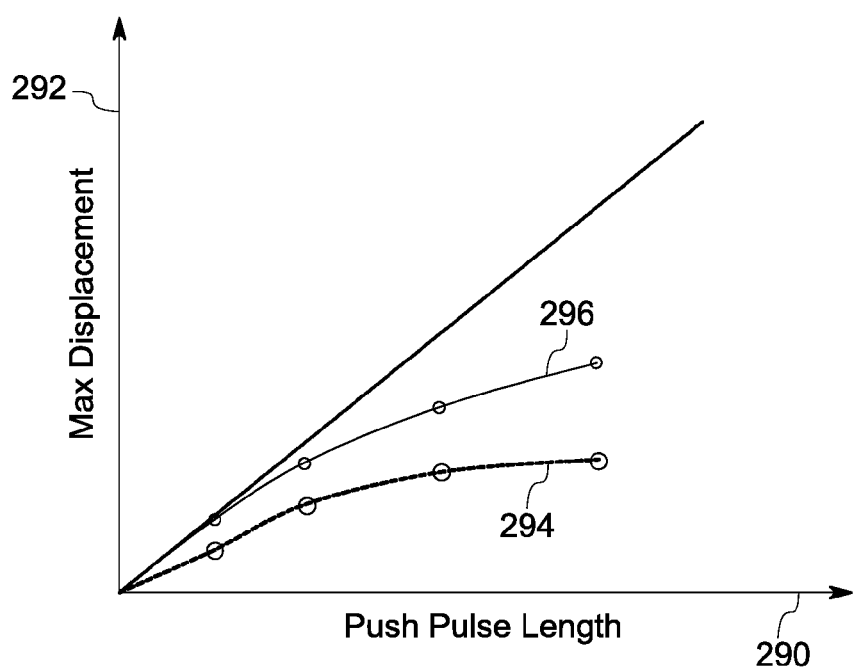

FIG. 16 is an example illustrating tissue discrimination based on the non-linear response. Abscissa 290 represents the length of the pushing pulse, and the ordinate 292 represents the maximum displacement of the target region for four pulse sequences delivered one at a time with the pushing pulse length being varied for each pulse sequence. In the illustrated embodiment, the curve 294 represents the displacement response of an invasive ductal carcinoma (IDC) or a cancerous tissue, and the curve 296 represent the displacement response of a healthy tissue. As illustrated, the IDC tissue is more non-linear than the underlying healthy tissue. Accordingly, diseased tissues can be distinguished from their healthy counterparts by characterizing which displacement curve the tissue follows.

Figure 17:
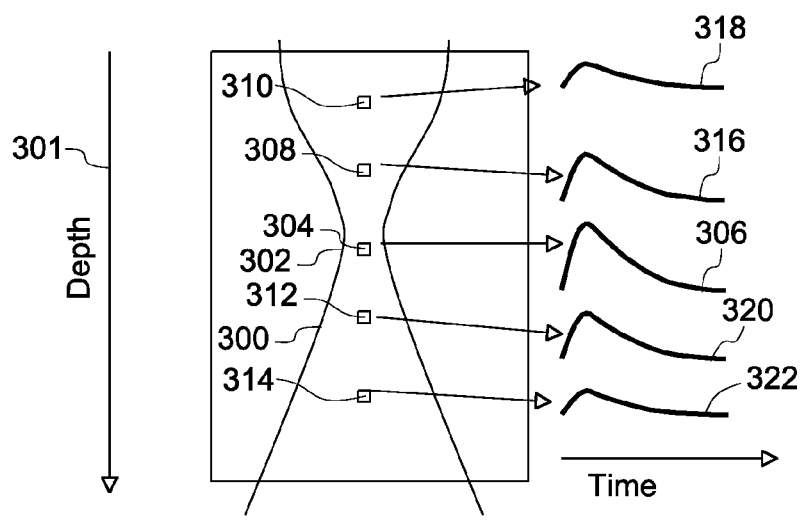
FIG. 17 is a schematic representation for depth dependence of the displacement response of the tissues, in accordance with embodiments of the present technique.

The displacement responses of the tissues discussed so far represent displacements at a particular point in space. However, for each tracking pulse that is delivered, displacements as a function of depth may be calculated. Since radiation force is proportional to the ultrasound intensity, and since the intensity varies over the depth of the transmitted pushing pulse, the radiation force may also vary over depth of the tissue in the medium. FIG. 17 illustrates an example of the depth dependence of the displacement response of the tissue in the target region. In order to generate images of the non-linear responses the depth dependence of the displacement response of the tissues should be accounted for. The arrow 301 represents the direction of increasing depth in the medium. As illustrated, for a given pushing pulse contour 300 having a determined pushing pulse length, the resulting force is largest at the focal depth 302 of the pushing pulse and drops off before and after this focus. Accordingly, the tissue 304 has a displacement curve 306 with the highest peak as compared to other tissues 308, 310, 312 and 314 having displacement curves 316, 318, 320 and 322, respectively. The displacement curves 306, 316, 318, 320 and 322 are drawn with abscissa as the time, and ordinate as the maximum displacement. The plot of maximum displacement of the tissue versus the pushing pulse variable parameter, such as length, for the different depths may look different even for a homogenous material. This is because the different depths are exposed to different push amplitudes for the same push pulse. As will be appreciated, both focusing and tissue attenuation will effect the radiation force experienced as a function of depth.

The depth dependent effects on the displacement response from the tissue may be addressed in various ways. In one embodiment, more than one focal zone may be used, with the assumption that near the focus the force is similar. By comparing different tissues from adjacent beams at the same depth and therefore, having similar force, the problem of depth dependence may be addressed. Although, the increased number of focal zones may result in increased tissue and transducer heating and reduced frame rate. Advantageously, the depth of field of the focus may be made large by increasing the f-number (ratio of the focal depth to aperture size). This allows the number of focal zones required to be decreased slightly. In another embodiment, phantom experiments may be used to calibrate the forces as a function of depth. The calibration of forces as a function of depth allows fewer transmits, while relying on the correction derived from the phantom data. In still another embodiment, the algorithms which process the recorded displacements could be more able. The models used to fit the data could include these effects.

Typically, there is dead time between the delivering of tracking pulse and starting of the next pulse sequence. In some embodiments, the reference pulses, pushing pulses and tracking pulses from the two or more target regions are interleaved so that the data from the two or more locations may be collected simultaneously. It should be noted that in these embodiments, each of the two or more target regions should be spaced far enough apart to minimize shear wave interaction between the target regions. Also, it is desirable that the target regions be located some distance apart to reduce tissue heating or reduce the time between deliveries, such that the next pulse sequence may be delivered without having to wait for the motion of the target region to return to equilibrium. In the illustrated embodiment of FIG. 18, pulse sequence 324 is delivered at a first target region, and the pulse sequence 326 is delivered at a second target region. As illustrated, the pulse sequence 324 includes a reference pulse 328, a pushing pulse 330, and tracking pulses 332. The pulse sequence 326 includes a reference pulse 334, a pushing pulse 336, and tracking pulses 338. The different pulses of the tracking pulses 324 and 326 are interleaved with respective pulses. For example, the reference pulses 328 and 334 are interleaved with one another to form the interleaved reference pulse 342, the pushing pulses 330 and 336 are interleaved with one another as indicated by the reference numeral 344, and the tracking pulses 332 and 338 are interleaved with one another as indicated by the reference numeral 346 of the pulse sequence 340. In the presently contemplated embodiment, reference pulse 328 is delivered at the first target region, followed by the reference pulse 334 that is delivered at the second target region. Next, the pushing pulse 330 is delivered at the first target region, followed by the pushing pulse 336 that is delivered at the second target region. Subsequently, the tracking pulse 332 is delivered at the first target region, followed by the tracking pulse 338 that is delivered at the second target region. Similarly, the subsequent pushing pulses and tracking pulses may be delivered successively at the two target regions. It should be noted that two or more pulse sequences may be interleaved.

Figure 19:
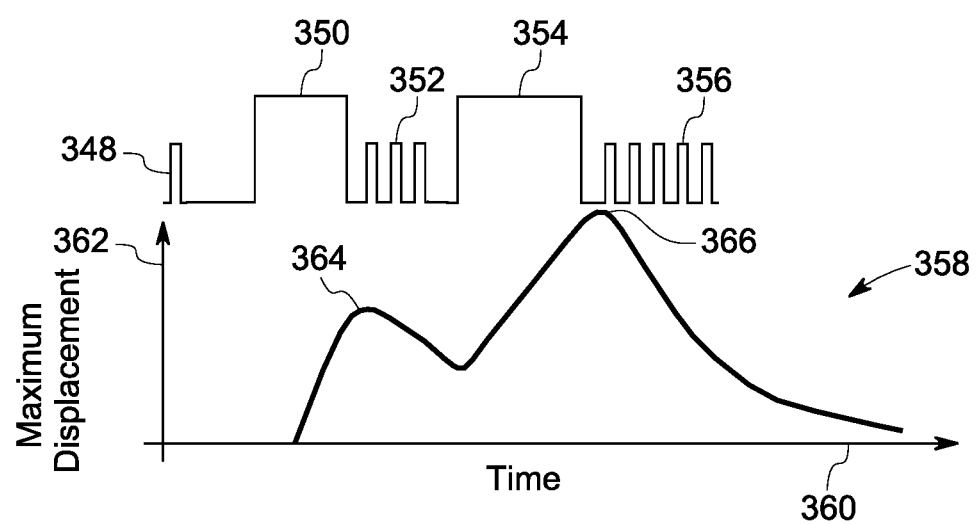
FIG. 19 is a drawing for delivering a pushing pulse to a target region before the relaxing of the tissues of the target region due to impact from the previous pushing pulse, in accordance with embodiments of the present technique.

In the illustrated embodiment of FIG. 19, displacement response of the tissue is illustrated for two subsequent pulse sequences. Initially, a reference pulse 348 is delivered to determine the initial location of the target region. Next, a pushing pulse 350 having a first value of the pulse length is delivered at the target region followed by tracking pulses 352. As illustrated by the graph 358 representing the relation between the maximum displacement (ordinate 362) with respect to time (abscissa 360), the first pushing pulse produces a maximum displacement 364 of the target region. A second pushing pulse 354 is delivered before the tissues of the target region relax from the impact of the first pushing pulse 350. The second pushing pulse 354 is delivered at the target region followed by the tracking pulse 356. Sending a pushing pulse at such shorter time intervals before waiting for the tissue to relax enables collection of more displacement values of the target region in a shorter period of time. The point 366 of the graph 358 illustrates the displacement of the target region as a result of the second pushing pulse 354.

In certain embodiments, a push pulse is delivered at a target region, which creates a shear wave that travels away from the push location. The resulting shear wave displacement response is tracked for one or more locations that are slightly away from the push region. The displacements generated by these shear waves will also be non-linear functions of the variable push pulse parameters. The resulting displacement of the tissues in the nearby locations may be ultrasonically tracked through time. The peak displacement or time-to-peak, or other parameters in response to the shear waves outside the region of excitation are used to characterize the material properties. In some embodiments, the wave properties of the shear waves may be altered. In these embodiments, amplitude, a peak power, a average power, a length, a frequency, a waveform, or combinations thereof, may be altered.

Figure 20:
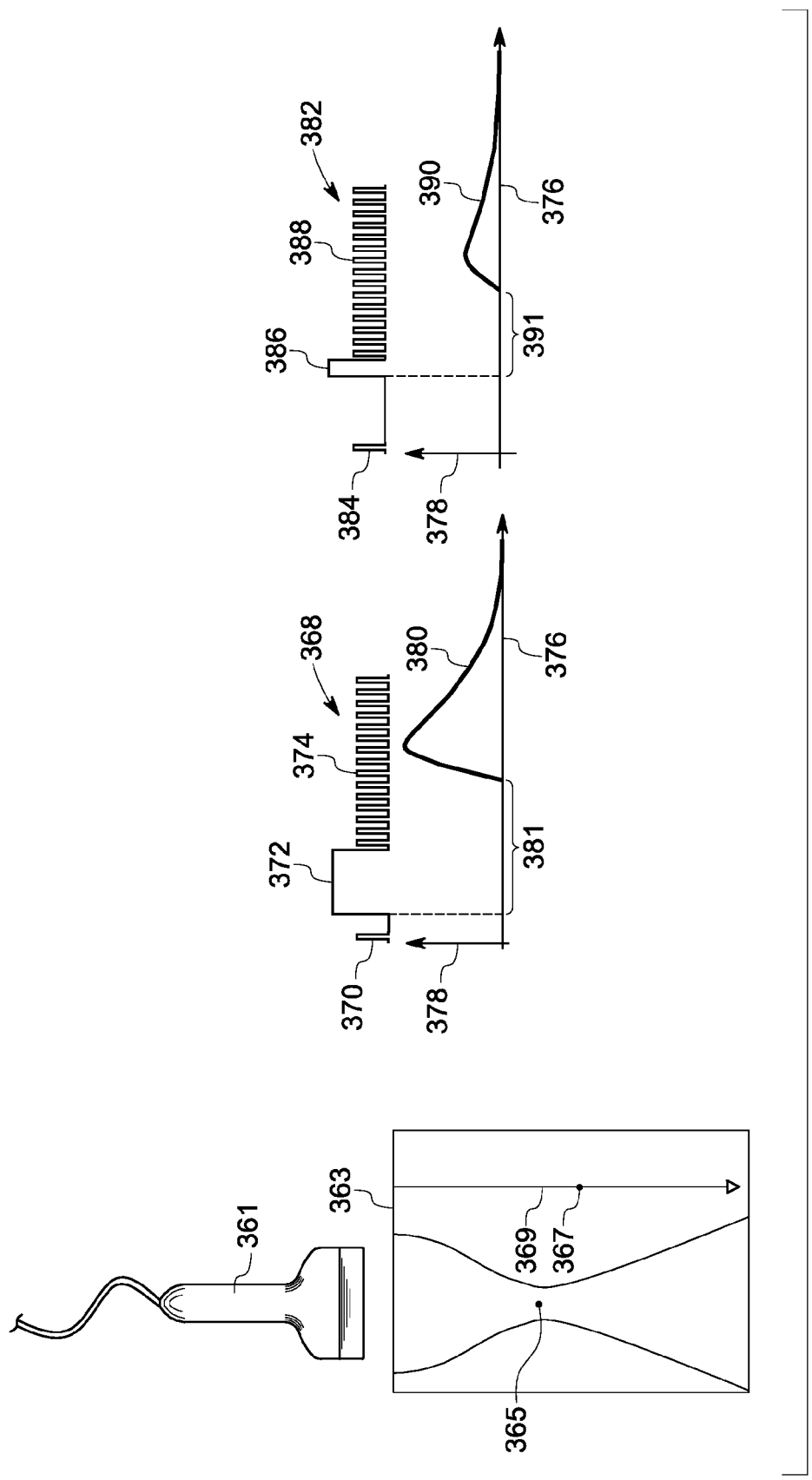
FIG. 20 is a schematic representation of displacements caused by shear waves created by pushing pulses with varying push parameters.

Turning now to FIG. 20, a transducer probe 361 configured to deliver pulse sequences 368 and 382 is disposed in close proximity to the object 363. The transducer probe 361 delivers pulse sequences 368 and 382 to a push location 365. In the illustrated embodiment, the pulse sequence 368 includes a reference pulse 370, a pushing pulse 372, which generates a corresponding shear wave (not shown), and tracking pulses 374. Similarly, the pulse sequence 382 includes a reference pulse 384, a pushing pulse 386, which generates a corresponding shear wave (not shown), and tracking pulses 388. In certain embodiments, pushing pulses having different values of variable parameters may produce corresponding shear waves that differ from each other in at least one wave property. In these embodiments, the non-linear parameters of the materials may be determined by creating shear waves with different wave properties and tracking corresponding displacements in the regions outside the tracking region. In the presently contemplated embodiment, the pushing pulse 386 has a shorter length than the pushing pulse 372. In the illustrated embodiment, the pulse sequences 368 and 382 are delivered at the push location 365, and the resultant maximum displacements caused by the corresponding shear waves are tracked at a separate location within the object 363 but outside the push location 365 are measured. The location 367 may or may not be at the same depth (represented by arrow 369) as the location 365, where the pulse sequences 368 and 382 are delivered. The graphs 380 and 390 drawn with abscissa 376 representing the time, and the ordinate 378 represent the displacement in the region 367 located outside the push location 365. As illustrated, there exists time delays 381 and 391 between the creation of the shear waves and tracking the displacement caused by the shear waves in the region 367 located outside the push location or target region 365.

In one embodiment, a response of the target region may include a displacement response, or a strain response, a strain-rate response, or a change in B-mode amplitude. It should be noted that many of the embodiments so far mentioned have relied on calculation of the displacements created by the pushing pulse. Given data from before a push and after a push it is possible to calculate the displacements and or strains. Non-limiting examples of techniques that may be employed to calculate the displacement response, the strain response, the strain-rate response, or the change in B-mode amplitude may include speckle tracking techniques, sum of absolute differences, iterative phase zeroing, direct strain estimators, cross-correlation, and auto-correlation techniques.

Although most of the embodiments describe displacement response of the tissue with respect to the pulse sequences. Other responses of the tissues such as strain, strain-rate, and change in the amplitude of the echoes of the tracking pulses may also be employed to study the tissue properties. After obtaining the data regarding the time and displacement for each target region, parameters related to the non-linear properties of the tissue may be calculated. Although there are numerous ways in which the non-linear parameter estimations may be done, an exemplary algorithm is described below.

In one embodiment, displacement responses of the tissue as a function of a variable pulse parameter, such as amplitude of the pushing pulse, are provided. The radiation force is depicted by Equation 1.

$$f = \alpha I/c \qquad \text{Equation 1}$$

where, f is the force per volume, I is the intensity of the sound, $\alpha$ is the absorption coefficient of the tissue, and c is the speed of sound in the tissue.

The force depicted in Equation 1 is the instantaneous body force. As the amplitude of the pushing pulse changes, the intensity of the acoustic radiation and thus the force changes. Therefore, plotting the displacement as a function of the square of the pushing pulse amplitude provides a function that is related to the displacement as a function of force.

Figure 21:
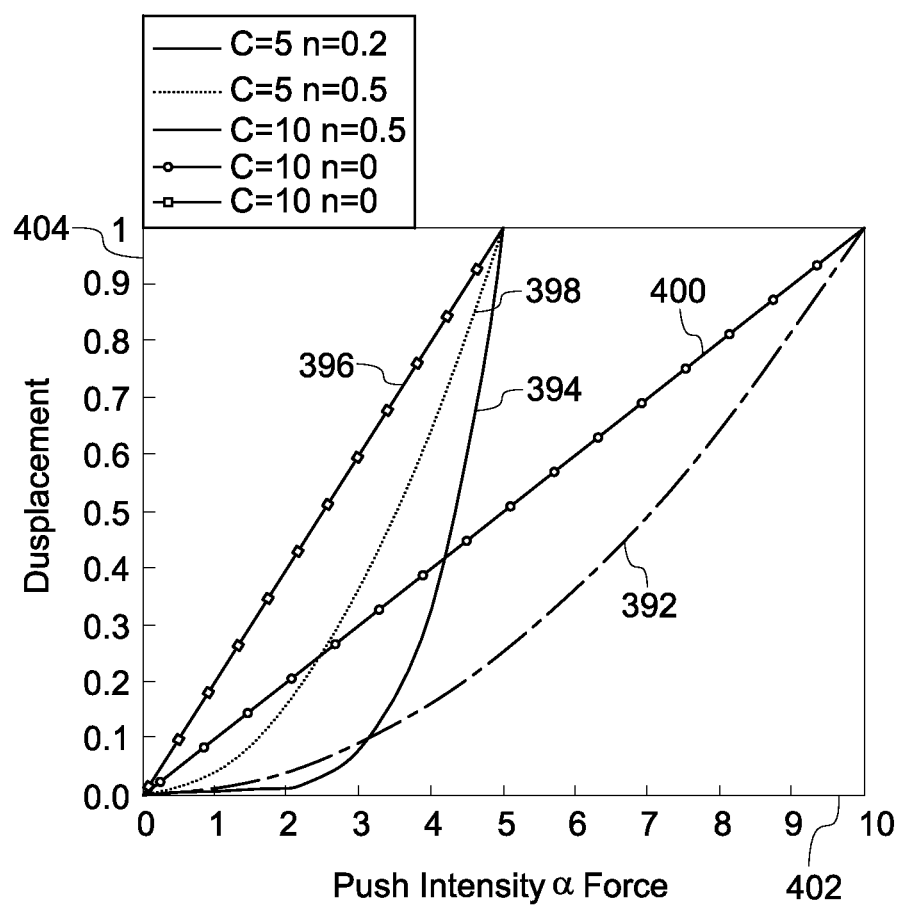
FIG. 21 is a graphical representation of estimating non-linear parameters of the tissue based on the displacement responses of the tissues, in accordance with embodiments of the present technique.

Next, the displacements versus pulse intensity is fitted to a function of the form give by Equation 2.

$$p = Cx^n \qquad \text{Equation 2}$$

where, p is the push intensity (proportional to the applied force), C is curve parameter, and n is a curve parameter, x is maximum displacement of the tissue. FIG. 21 illustrates members of this family of curves 392, 394, 396, 398 and 400 with abscissa 402 representing the push force (f), and the ordinate 404 representing the displacement of the tissue. The C and n parameters can then be made into images that may provide contrast.

In another embodiment, the displacement is given by a function of the form represented in Equation 3.

$$x = \alpha p + \beta p^2 O^3 \qquad \text{Equation 3}$$

where, p is the intensity of the push pulse, x is maximum displacement of the tissue, $\alpha$ and $\beta$ are curve fitting parameters, the linear term coefficient and the square term coefficient. $O^3$ represents higher order terms of p cubed and more. Standard regression techniques may be used to find $\alpha$ and $\beta$.

In one embodiment, a FEM model may be employed to fit the data. The FEM model would attempt to determine the underlying material constants. In another embodiment, a simpler model is made to fit the data collected. There are several simplified models of non-linear elasticity. Each model has its own set of parameters or physical properties that must be chosen to match the acquired data. Fitting the model implies finding a set of model parameters that produce the measured results. These parameters may then be used as imaging functional.

In each of these examples the intensity of the push pulse was used, but other parameters that are varied may also be used, such as pulse length.

Once the non-linear parameters have been calculated or determined from the data, it is possible to generate images of one or several parameters. In one embodiment, a function of the parameters may be made into an image. In one example, if Equation 2 is used to fit the data, an image of the parameter C and an image of parameter n may be made. In another example, if Equation 3 is used to fit the data, then images of $\alpha$ or $\beta$ may be made.

Figure 22:
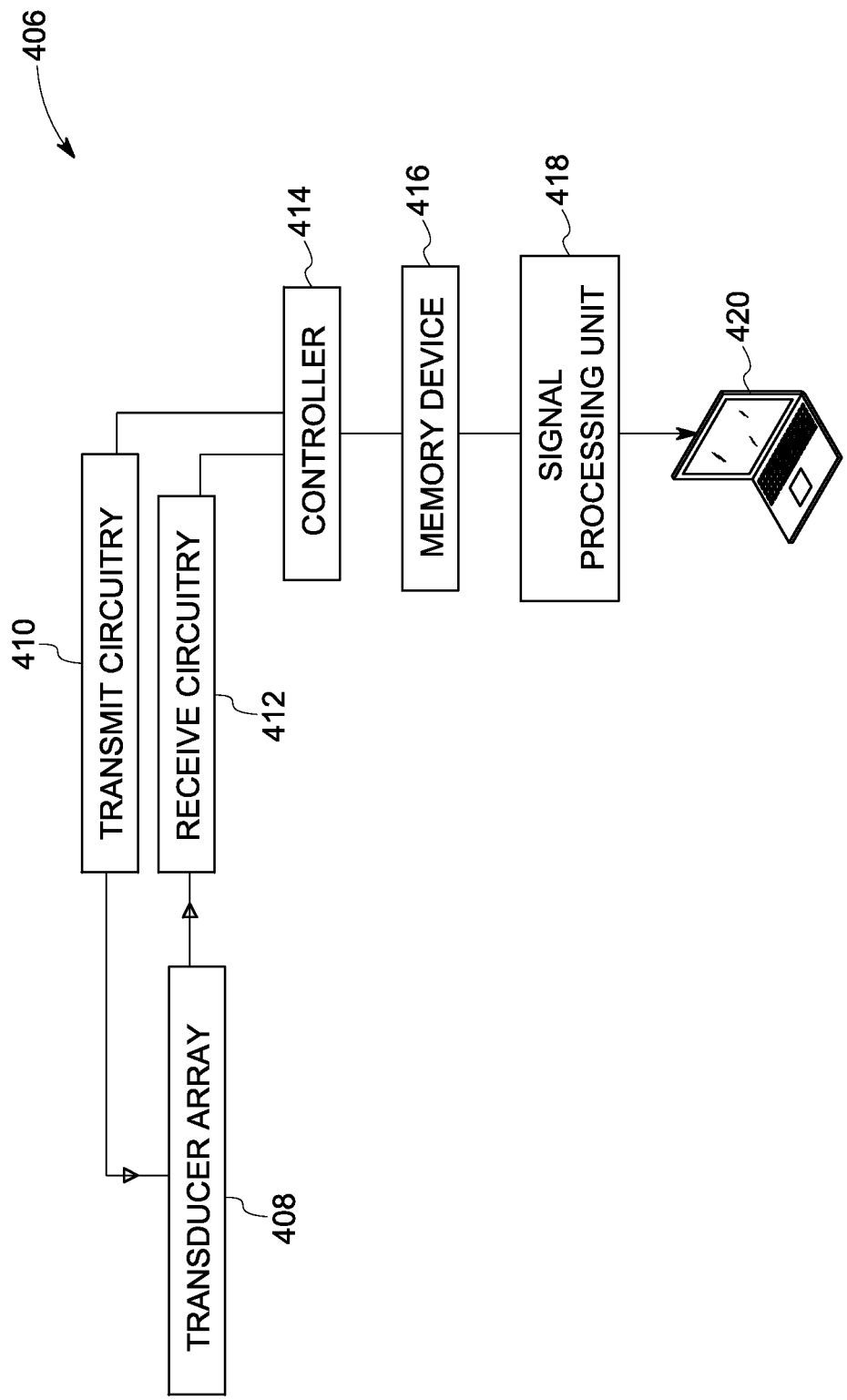
FIG. 22 is a schematic representation of an ultrasound imaging system for imaging regions of altered stiffness, in accordance with embodiments of the present technique.

FIG. 22 illustrates an ultrasound imaging system 406 having a transducer array 408. The transducer array 408 may be a one-dimensional or a two-dimensional array. The transducer array 408 may be directed to a two-dimensional plane comprising one or more target regions. The reference pulse, pushing pulse, and the tracking pulse may be delivered using the transducer array 408. Typically, the transducer array 408 is in physical contact with the subject while delivering the pulses. A transmit circuitry 410 for delivering the pulses is in operative association with the transducer array 408. A receive circuitry 412 is in operative association with the transducer array to receive information from the target regions. Both the transmit circuitry 410 and the receive circuitry 412 are electronically coupled to a controller 414. The controller 414 controls the pulse sequence, variable parameter of the pushing pulse, and other variables such as PRF of the tracking pulse, time of delivery of the tracking pulse after the delivery of the pushing pulse. Further, the controller 414 also organizes information received from the tracking regions. The information received from the target region may be stored in the memory device 416 to be processed later in time. In one example, the memory device 416 may include a random access memory, however, other memory devices may be used. The memory device 416 may be used to store information such as initial position of the target region, and displaced position of the target region. A signal-processing unit 418 then processes the information stored in the memory device 416. Alternatively, the signal-processing unit may directly use the information from the controller 414 to generate images for the target regions. The processed image is displayed using a display device 420, such as a monitor. Although not illustrated, a measuring device for point measurement of a displacement of the target region may be employed in place of the display device 420. Certain elements shown in FIG. 22 may be omitted or the functionality of certain elements may be combined with other elements. For example, the signal-processing unit 418 may be provided as part of the controller 414.

Generally, the present technique may be employed to assess mechanical properties of tissue or any other material that is suitable for ultrasound imaging and that may be subjected to acoustic radiation of the ultrasound imaging. For example, the characterization of arterial stiffness, which can be indicative of the degree of atherosclerotic disease, the assessment of muscle tone, which is of importance in determining the course of treatment for female pelvic floor complications, and assessing the stiffness of kidneys, which can be indicative of the viability of kidney transplants. Further, the present technique may be carried out on human subjects for diagnostic or prognostic purposes, and may be carried out on animal subjects such as dogs and cats for veterinary purposes. The present technique could also be useful in radio frequency (RF) ablation therapy for liver cancer, in which the progress of the therapy could be monitored real-time.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An ultrasound imaging method for detecting a target region of altered stiffness, comprising:
   delivering at least one reference pulse to the target region to detect an initial position of the target region;
   delivering a first pushing pulse having a first value of a variable parameter to the target region to displace the target region to a first displaced position;
   delivering a first tracking pulse to detect the first displaced position of the target region;
   delivering a second pushing pulse having a second value of the variable parameter to the target region to displace the target region to a second displaced position;
   delivering a second tracking pulse to detect the second displaced position of the target region; and
   detecting the target region of altered stiffness based on the first displaced position and the second displaced position of the target region.

2. The method of claim 1, wherein the first pushing pulse and the second pushing pulse are delivered to the target region and at least one other target region.

3. The method of claim 1, wherein the variable parameter of the pushing pulse comprises an amplitude, a peak power, an average power, a length, a frequency, a waveform, pulse repetition frequency, or combinations thereof.

4. The method of claim 3, further comprising mapping displacements of the target region with respect to the variable parameter.

5. The method of claim 1, wherein the first or second tracking pulses are, respectively, delivered after a motion induced by the first or second pushing pulses is reduced to a determined value.

6. The method of claim 1, further comprising interleaving one or more of the reference pulse, the tracking pulse, or the pushing pulses for the target region and at least one other target region.

7. The method of claim 1, wherein at least one of the first and second pushing pulses is delivered as a plurality of pulses.

8. The method of claim 7, wherein the first tracking pulse, or the second tracking pulse, or both, are delivered in between the plurality of pulses of the first or the second pushing pulse.

9. The method of claim 1, wherein at least one of the first and second pushing pulses is delivered to the target region while varying two or more variable parameters of at least one of the first and second pushing pulses.

10. The method of claim 9, wherein the first and second pushing pulses are delivered at the target region while successively changing the variable parameter before moving to at least one other target region.

11. The method of claim 10, further comprising:
    delivering the first and second pushing pulses having the first value of the variable parameter to the target region and the at least one other target region and changing the value of the variable parameter of the first and second pushing pulses to the second value; and
    delivering the first and second pushing pulses having the second value of the variable parameter to the target region and the at least one other target region.

12. The method of claim 1, further comprising varying pulse repetition frequency (PRF) of the first tracking pulse, or the second tracking/pushing pulse, or both.

13. The method of claim 1, further comprising measuring at least one of a maximum displacement, a time-to-peak displacement, a time to recover from peak displacement to a determined value, an integral under the displacement curve, or a displacement at a determined time for the target region as a function of the variable parameter.

14. The method of claim 1, further comprising delivering another reference pulse prior to delivering the second pushing pulse.

15. The method of claim 1, further comprising delivering at least a pair of pushing pulses, wherein one of the pair of pushing pulses comprises a first variable parameter, and the other of the pair of pushing pulses comprises a second variable parameter, and wherein one of the first and second variable parameters is taken as a reference.

16. A method of detecting a target region of altered stiffness, comprising:
    delivering pushing pulses at the target region while varying a variable parameter of the pushing pulses;
    tracking displacements in one or more regions disposed outside the target region; and
    detecting the target region of altered stiffness based on the displacements in the one or more regions disposed outside the target region.

17. The method of claim 16, further comprising measuring at least one of a maximum displacement, a time-to-peak displacement, a time to recover from peak displacement to a determined value, an integral under a displacement curve, or a displacement at a determined time for the target region as a function of the variable parameter of the pushing pulses.

* * * * *